US010506917B2

(12) United States Patent
Adachi

(10) Patent No.: US 10,506,917 B2
(45) Date of Patent: Dec. 17, 2019

(54) ENDOSCOPE AND ENDOSCOPE SYSTEM WITH TRANSMISSION BUFFER

(71) Applicant: OLYMPUS CORPORATION, Tokyo (JP)

(72) Inventor: Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 307 days.

(21) Appl. No.: 15/432,123

(22) Filed: Feb. 14, 2017

(65) Prior Publication Data

US 2017/0150869 A1  Jun. 1, 2017

Related U.S. Application Data

(63) Continuation of application No. PCT/JP2016/055573, filed on Feb. 25, 2016.

(30) Foreign Application Priority Data

Apr. 16, 2015 (JP) .................................. 2015-084315

(51) Int. Cl.
*A61B 1/00* (2006.01)
*A61B 1/04* (2006.01)
(Continued)

(52) U.S. Cl.
CPC ...... *A61B 1/00029* (2013.01); *A61B 1/00006* (2013.01); *A61B 1/00009* (2013.01); *A61B 1/00114* (2013.01); *A61B 1/051* (2013.01)

(58) Field of Classification Search
CPC ............ A61B 1/00029; A61B 1/00006; A61B 1/00009; A61B 1/00114; A61B 1/04; A61B 1/051; G02B 23/2484; H04N 5/378
(Continued)

(56) References Cited

U.S. PATENT DOCUMENTS 4,349,014 A * 9/1982 Takamatsu ......... A61B 1/00055
396/17
5,113,254 A * 5/1992 Kanno ................. H04N 5/2251
348/242

(Continued)

FOREIGN PATENT DOCUMENTS

JP  2003-153858 A  5/2003
JP  2014-036724 A  2/2014

(Continued)

OTHER PUBLICATIONS

International Search Report dated May 24, 2016 issued PCT/JP2016/055573.

(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

An endoscope configured to operate with a power supply voltage supplied from a processing device connected to the endoscope through a transmission cable is provided. The endoscope includes: a first chip including: an imaging element; and a first buffer configured to externally output an imaging signal generated by the imaging element; and a second chip including a second buffer configured to amplify the imaging signal output from the first buffer and output the amplified imaging signal to the transmission cable. The first buffer is configured to apply a predetermined voltage to the second buffer in a period in which the imaging element does not output the imaging signal to cause the second buffer to output a direct current at a predetermined level to the transmission cable.

7 Claims, 4 Drawing Sheets

(51) Int. Cl.
*A61B 1/05* (2006.01)
*G02B 23/24* (2006.01)
*H04N 5/378* (2011.01)
*H04N 5/225* (2006.01)

(58) Field of Classification Search
USPC ............... 600/109, 110, 111, 112, 132, 160; 348/65, 68
See application file for complete search history.

(56) References Cited

U.S. PATENT DOCUMENTS

| | | | | |
|---|---|---|---|---|
| 5,278,656 | A * | 1/1994 | Hynecek | H04N 5/335 348/207.99 |
| 5,374,953 | A * | 12/1994 | Sasaki | A61B 1/05 348/65 |
| 2002/0021355 | A1* | 2/2002 | Utsui | A61B 1/0638 348/65 |
| 2008/0143826 | A1* | 6/2008 | Shibasaki | A61B 1/045 348/65 |
| 2013/0088628 | A1* | 4/2013 | Itano | H04N 5/3658 348/308 |
| 2014/0078335 | A1* | 3/2014 | Kobayashi | H04N 5/376 348/222.1 |
| 2014/0300717 | A1 | 10/2014 | Yokohama | |
| 2014/0320618 | A1* | 10/2014 | Akahane | H04N 5/363 348/65 |
| 2015/0144771 | A1* | 5/2015 | Hagihara | H03M 1/56 250/208.1 |
| 2015/0342443 | A1 | 12/2015 | Tanabe et al. | |
| 2015/0381866 | A1* | 12/2015 | Ono | H04N 5/2256 348/68 |
| 2016/0022117 | A1 | 1/2016 | Akahane et al. | |
| 2016/0119528 | A1* | 4/2016 | Adachi | A61B 1/04 348/68 |
| 2016/0206186 | A1* | 7/2016 | Igarashi | A61B 1/0008 |
| 2016/0209637 | A1* | 7/2016 | Fujimori | A61B 1/051 |

FOREIGN PATENT DOCUMENTS

| | | |
|---|---|---|
| WO | 2014/171308 A1 | 10/2014 |
| WO | 2014/175005 A1 | 10/2014 |
| WO | 2014/175006 A1 | 10/2014 |
| WO | 2016/006302 A1 | 1/2016 |

OTHER PUBLICATIONS

Extended Supplementary European Search Report dated Mar. 21, 2018 in European Patent Application No. 16 77 9825.5.

\* cited by examiner

US 10,506,917 B2

ENDOSCOPE AND ENDOSCOPE SYSTEM WITH TRANSMISSION BUFFER

CROSS-REFERENCE TO RELATED APPLICATIONS

This application is a continuation of PCT international application Ser. No. PCT/JP2016/055573 filed on Feb. 25, 2016 which designates the United States, incorporated herein by reference, and which claims the benefit of priority from Japanese Patent Application No. 2015-084315, filed on Apr. 16, 2015, incorporated herein by reference.

BACKGROUND

1. Technical Field

The disclosure relates to an endoscope inserted into a subject, imaging within the body of the subject, and generating image data, and an endoscope system.

2. Related Art

A technique is known wherein an imaging element such as a charge coupled device (CCD) or a complementary metal oxide semiconductor (CMOS) at a distal end of an insertion section of an endoscope, and an amplifier provided in the vicinity of the imaging element amplify an imaging signal output from the imaging element, and output the imaging signal to a processor (see JP 2003-153858 A). According to this technique, a pulse signal for driving the imaging element is used to generate a DC voltage applied to the imaging element and the amplifier, thereby reducing the number of power supply cables to reduce a diameter of the insertion section of the endoscope.

SUMMARY

In some embodiments, an endoscope configured to operate with a power supply voltage supplied from a processing device connected to the endoscope through a transmission cable is provided. The endoscope includes: a first chip including: an imaging element; and a first buffer configured to externally output an imaging signal generated by the imaging element; and a second chip including a second buffer configured to amplify the imaging signal output from the first buffer and output the amplified imaging signal to the transmission cable. The first buffer is configured to apply a predetermined voltage to the second buffer in a period in which the imaging element does not output the imaging signal to cause the second buffer to output a direct current at a predetermined level to the transmission cable.

In some embodiments, an endoscope system includes: the above-described endoscope; and a processing device including a drive signal generating unit configured to transmit a drive signal to the imaging element through the transmission cable, an image signal processing unit configured to receive the imaging signal amplified by the second buffer through the transmission cable, and a power supply unit configured to supply a power supply voltage to the imaging element, the first chip, and the second chip.

DETAILED DESCRIPTION

An endoscope system including an endoscope with a distal end to be inserted into a subject will be described as a mode for carrying out the present invention (hereinafter referred to as "embodiment"). The present invention is not limited to this embodiment. Furthermore, in the description of the drawings, the same portions are denoted by the same reference signs. Still furthermore, it should be noted that the drawings are schematically illustrated, and relationships between the thicknesses and the widths, the proportions, or the like of members may be different from those of actual ones. In addition, the drawings include a portion which is different in size or proportion between the drawings.

Configuration of Endoscope System

Figure 1:
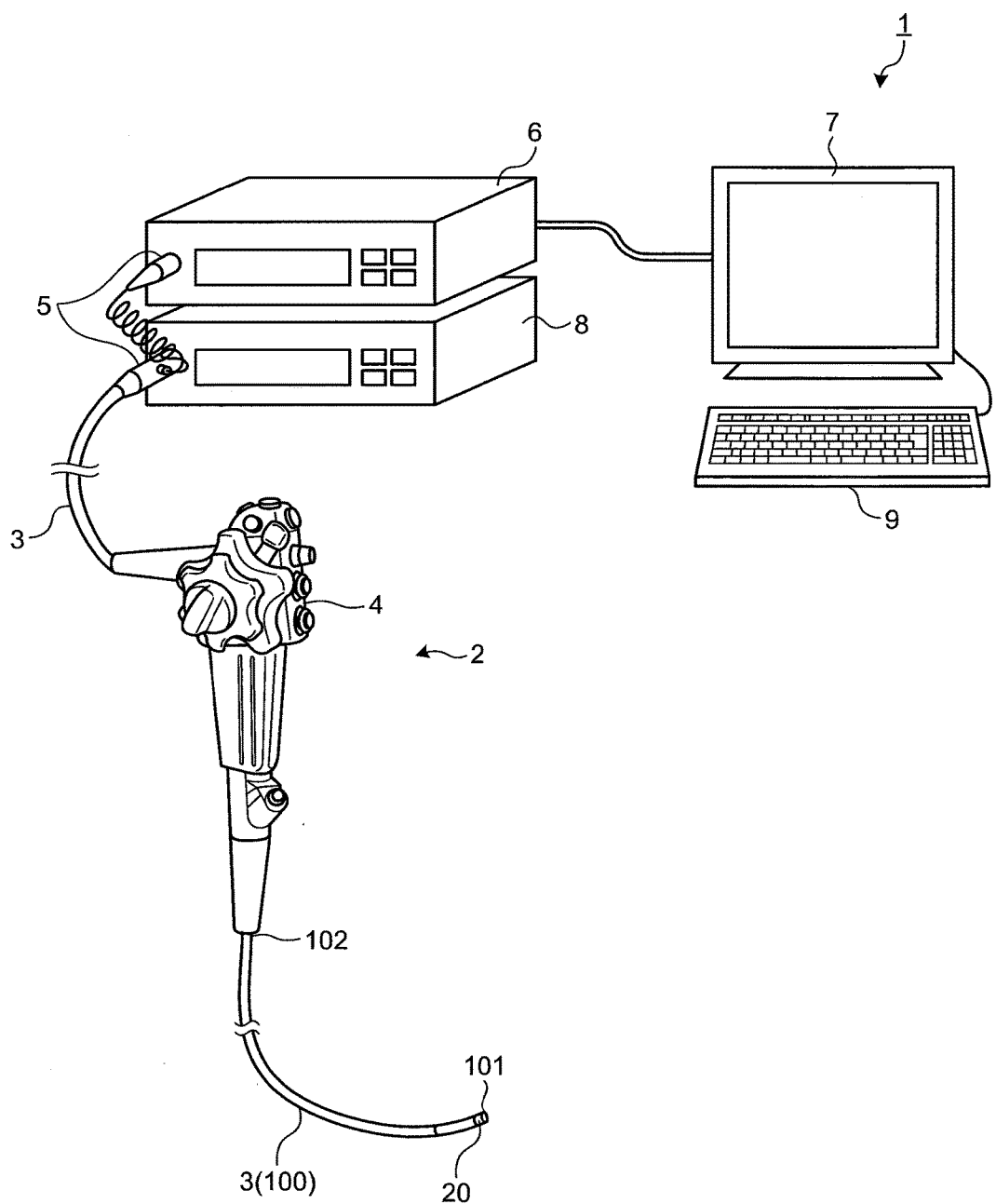
FIG. 1 is a schematic view illustrating an overall configuration of an endoscope system according to an embodiment of the disclosure.

FIG. 1 is a schematic view illustrating an overall configuration of the endoscope system according to an embodiment of the disclosure. An endoscope system 1 illustrated in FIG. 1 includes an endoscope 2, a transmission cable 3, a connector portion 5, a processor 6 (processing device), a display device 7, a light source device 8, and an input unit 9.

The endoscope 2 outputs an imaging signal (image data) to the processor 6 by capturing an in-vivo image of the subject using an insertion section 100, which is a part of the transmission cable 3, inserted into a body of the subject. Furthermore, in the endoscope 2, an imaging unit 20 (imaging device) capturing the in-vivo image is provided, at one end of the transmission cable 3, on the side of a distal end 101 of the insertion section 100 to be inserted into a body cavity of the subject, and an operating unit 4 receiving various operations with respect to the endoscope 2 is connected on the side of a proximal end 102 of the insertion section 100. The imaging unit 20 is connected to the connector portion 5 through the operating unit 4 by the transmission cable 3. The Imaging signal of the image captured by the imaging unit 20 passes through, for example, the transmission cable 3 having a length of several meters, and is output to the connector portion 5. It should be noted that in the present embodiment, the endoscope 2 functions as the imaging device.

The transmission cable 3 connects the endoscope 2 and the connector portion 5 to each other, and connects the endoscope 2 and the light source device 8 to each other. The transmission cable 3 transmits the imaging signal generated by the imaging unit 20 to the connector portion 5. The transmission cable 3 includes a cable, an optical fiber, or the like.

The connector portion 5 is connected to the endoscope 2, the processor 6, and the light source device 8, performs predetermined signal processing on the imaging signal output from the endoscope 2 connected thereto, and performs analog-to-digital conversion (A/D conversion) on the imaging signal, and outputs the converted imaging signal as an image signal to the processor 6.

The processor 6 performs predetermined image processing on the image signal output from the connector portion 5, and generally controls the whole endoscope system 1. It should be noted that in the present embodiment, the processor 6 functions as the processing device.

The display device 7 displays an image corresponding to the image signal subjected to the image processing by the processor 6. The display device 7 displays various information about the endoscope system 1. The display device 7 includes a liquid crystal or organic electro luminescence (EL) display panel.

The light source device 8 includes, for example, a halogen lamp or a white light emitting diode (LED), and emits illumination light to the subject from the distal end side of the insertion section 100 of the endoscope 2, through the connector portion 5 and the transmission cable 3.

The input unit 9 includes, for example, a keyboard or a mouse, and receives input of information about various operations for the endoscope system 1. For example, the input unit 9 receives input of an instruction signal for instructing amplification (gain-up) of the imaging signal from the endoscope 2 or a light intensity of the light source device 8.

Figure 2:
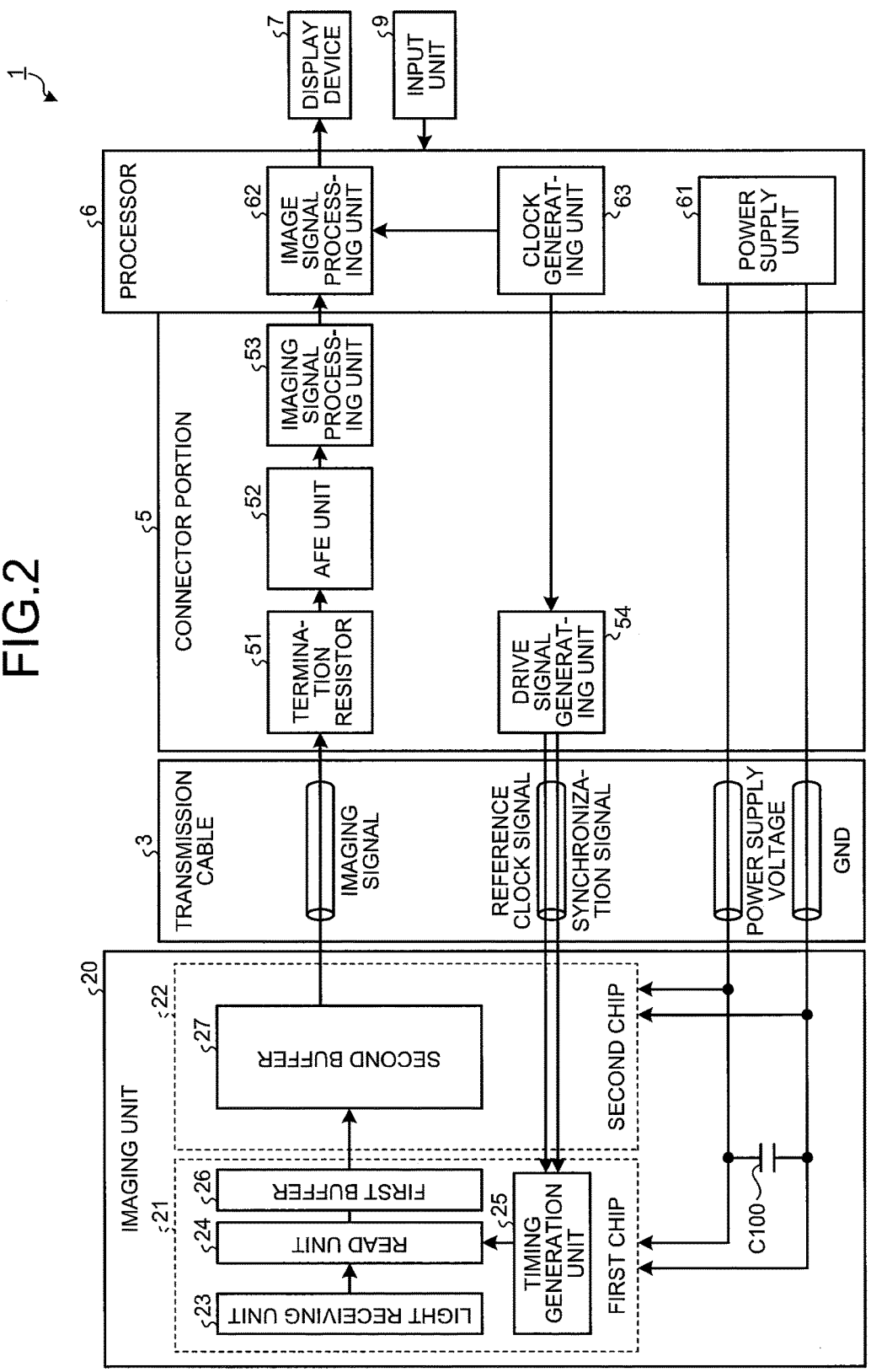
FIG. 2 is a block diagram illustrating a function of a main portion of the endoscope system according to an embodiment of the disclosure.

FIG. 2 is a block diagram illustrating a function of a main portion of the endoscope system 1. A detailed configuration of each unit of the endoscope system 1 and an electrical signal path in the endoscope system 1 will be described with reference to FIG. 2. As illustrated in FIG. 2, the imaging unit 20 has a first chip 21 (imaging element), and a second chip 22.

The first chip 21 includes a light receiving unit 23 including a plurality of pixels arranged in a two-dimensional matrix, receiving external light, and generating and outputting the imaging signal according to an amount of light received, a read unit 24 reading the imaging signal obtained by photoelectrical conversion by the light receiving unit 23, a timing generation unit 25 generating a timing signal based on a reference clock signal and a synchronization signal input from the connector portion 5, and outputting the timing signal to the read unit 24, and a first buffer 26 amplifying the imaging signal read from the light receiving unit 23 by the read unit 24 and applying a predetermined voltage to a second buffer 27 of the second chip 22 in a period in which the read unit 24 does not output the imaging signal read from the light receiving unit 23 to cause the second buffer 27 to output a direct current at a predetermined level to the transmission cable 3. It should be noted that a more detailed configuration of the first buffer 26 will be described later with reference to FIG. 3. It should be noted that in the present embodiment, the light receiving unit 23 and the read unit 24 function as the imaging element.

The second chip 22 includes the second buffer 27 amplifying the imaging signal output from each of the pixels in the first chip 21, and outputting the amplified imaging signal to the transmission cable 3. It should be noted that a more detailed configuration of the second chip 22 will be described later with reference to FIG. 3.

In addition, the imaging unit 20 receives a power supply voltage VDD generated by a power supply unit 61 in the processor 6, and a ground (GND), through the transmission cable 3. A capacitor C100 for stabilizing power supply is provided between the power supply voltage VDD and the ground (GND) supplied to the imaging unit 20.

The connector portion 5 electrically connects the endoscope 2 (imaging unit 20) and the processor 6 to each other to function as a relay processing unit for relaying an electrical signal. The connector portion 5 and the imaging unit 20 are connected by the transmission cable 3, and the connector portion 5 and the processor 6 are connected by a coiled cable. The connector portion 5 is also connected to the light source device 8. The connector portion 5 includes a termination resistor 51, an analog front end unit 52 (hereinafter, referred to as "AFE unit 52"), an imaging signal processing unit 53, and a drive signal generating unit 54.

The termination resistor 51 is provided at an end of the transmission cable 3. It should be noted that a more detailed configuration of the termination resistor 51 will be described later with reference to FIG. 3.

The AFE unit 52 receives the imaging signal transmitted from the imaging unit 20, performs impedance matching using a passive element such as a resistor, extracts an AC component in the capacitor, and then determines an operating point in a voltage divider. The AFE unit 52 performs A/D conversion on an analog imaging signal transmitted from the imaging unit 20, and outputs the converted analog imaging signal to the imaging signal processing unit 53 as a digital imaging signal.

The imaging signal processing unit 53 performs predetermined signal processing, such as vertical line removal or noise removal, on the digital imaging signal input from the AFE unit 52, and outputs the imaging signal performed the predetermined signal processing to the processor 6. The imaging signal processing unit 53 includes, for example, a field programmable gate array (FPGA).

On the basis of the reference clock signal (for example, a clock signal of 27 MHz) transmitted from the processor 6, and serving as a reference of the operation of each component unit of the endoscope 2, the drive signal generating unit 54 generates the synchronization signal indicating a starting position of each frame, and outputs the synchronization signal to the timing generation unit 25 of the imaging unit 20, through the transmission cable 3, together with the reference clock signal. Here, the synchronization signal generated by the drive signal generating unit 54 includes a horizontal synchronization signal and a vertical synchronization signal.

Processor 6 is a control device performing overall control of the whole endoscope system 1. The processor 6 includes the power supply unit 61, an image signal processing unit 62, and a clock generating unit 63.

The power supply unit 61 generates the power supply voltage VDD, and supplies the generated power supply voltage VDD and the ground (GND) to the imaging unit 20 through the connector portion 5 and the transmission cable 3.

The image signal processing unit 62 performs image processing, such as synchronization processing, white balance (WB) adjustment, gain adjustment, gamma correction, digital to analog (D/A) conversion, or format conversion, on the digital imaging signal subjected to the signal processing by the imaging signal processing unit 53 to convert into the image signal, and outputs the converted image signal to the display device 7.

The clock generating unit 63 generates the reference clock signal serving as a reference of the operation of each component unit of the endoscope system 1, and outputs this reference clock signal to the AFE unit 52, the imaging signal processing unit 53, the drive signal generating unit 54, and the image signal processing unit 62.

Configurations of First Buffer, Second Buffer, and Termination Resistor

Figure 3:
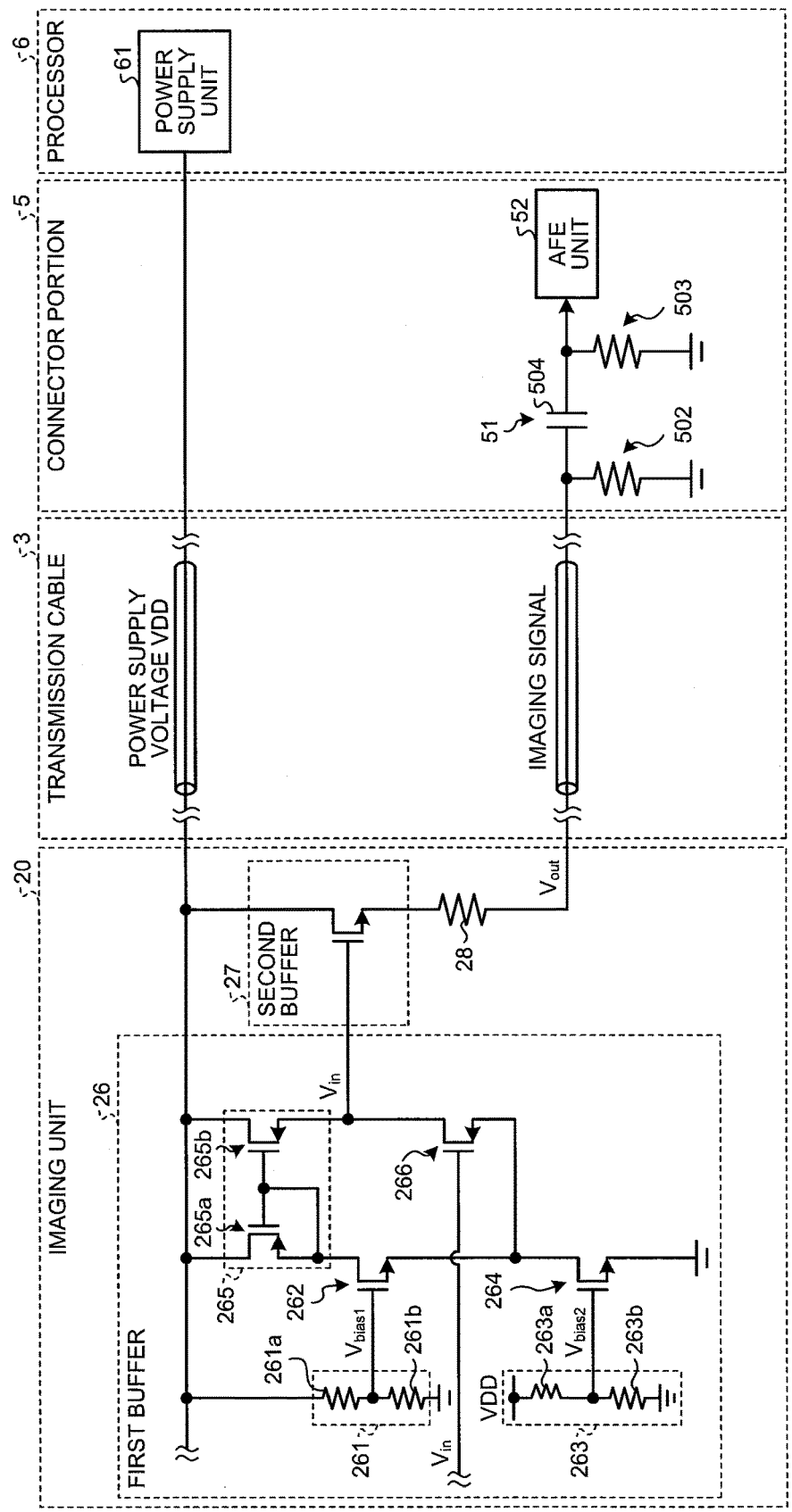
FIG. 3 is a circuit diagram illustrating detailed configurations of a first buffer, a second buffer, and a termination resistor illustrated in FIG. 2.

Next, the detailed configurations of main portions of the first buffer 26, the second buffer 27, and the termination resistor 51 will be described. FIG. 3 is a circuit diagram illustrating the detailed configurations of the first buffer 26, the second buffer 27, and the termination resistor 51 illustrated in FIG. 2.

As illustrated in FIG. 3, the first buffer 26 applies a voltage obtained by dividing the power supply voltage VDD supplied from the power supply unit 61 of the processor 6 through the transmission cable 3, to the second buffer 27. The first buffer 26 includes a first voltage divider 261, a first transistor 262, a second voltage divider 263, a second transistor 264, a current mirror circuit 265, a third transistor 266.

The first voltage divider 261 includes a first resistor 261a and a second resistor 261b connected in series between the power supply voltage VDD and the ground, and applies a divided output voltage Vbias1 to a gate of the first transistor 262.

The first transistor 262 includes an NMOS transistor. In the first transistor 262, the current mirror circuit 265 is connected to a drain, the third transistor 266 is connected to a source, and a connecting line receiving application of the output voltage Vbias1 from the first voltage divider 261 is connected to a gate.

The second voltage divider 263 includes a third resistor 263a and a fourth resistor 263b connected in series between the power supply voltage VDD and the ground, and applies a divided output voltage Vbias2 to a gate of the second transistor 264.

The second transistor 264 includes an NMOS transistor. In the second transistor 264, the third transistor 266 is connected to a drain, the ground is connected to a source, and a connecting line receiving application of the output voltage Vbias2 from the second voltage divider 263 is connected to a gate.

The current mirror circuit 265 duplicates a current determined using on-resistance of the first transistor and the second transistor, from a fourth transistor 265a to a fifth transistor 265b.

The fourth transistor 265a includes a PMOS transistor. In the fourth transistor 265a, the power supply voltage VDD is connected to a source, and the drain of the first transistor 262 is connected to a drain.

The fifth transistor 265b includes a PMOS transistor. In the fifth transistor 265b, the power supply voltage VDD is connected to a source, the third transistor 266 is connected to a drain, and the drain side of the first transistor 262 is connected to a gate.

The third transistor 266 includes a PMOS source follower transistor. In the third transistor 266, a constant current source is connected, and the constant current source is driven by a divided voltage divided by the current mirror circuit 265 where the current determined using the first voltage divider 261 and the second voltage divider 263 is applied. The current mirror circuit 265 where the current determined using the first voltage divider 261 and the second voltage divider 263 is applied is connected to a source side. Furthermore, the second buffer 27 is connected to an output end (source side), and a connecting line transmitting the imaging signal Vin read from the light receiving unit 23 by the read unit 24 is connected to an input end (gate side).

The second buffer 27 includes an NMOS transistor. In the second buffer 27, the power supply voltage VDD is connected to a drain, the transmission cable 3 externally transmitting the imaging signal Vout through an impedance resistor 28 for matching impedance of the transmission cable 3 is connected to an output end (source side), and a signal line transmitting the imaging signal Vin output from the first chip 21 is connected to an input end (gate side).

The connector portion 5 includes at least an AC termination resistor 503 connected to the GND, a DC termination resistor 502 connected to the GND, and a DC decoupling capacitor 504 decoupling the direct current output from the second chip 22.

Figure 4:
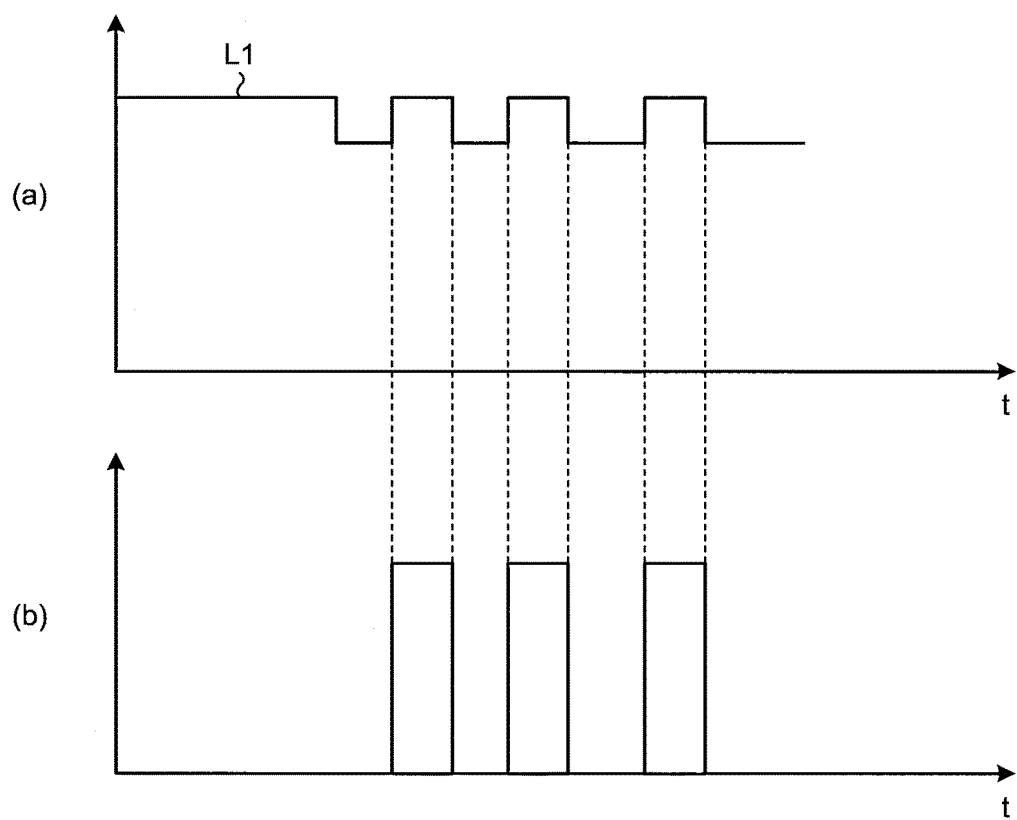
FIG. 4 is a schematic view illustrating change in current output from the second buffer.

Next, the change in current output from the second buffer 27 will be described. FIG. 4 is a schematic view illustrating the change in current output from the second buffer 27. In FIG. 4, the horizontal axis represents time, and the vertical axis represents values of current. Furthermore, (a) of FIG. 4 represents the values of current output from the second buffer 27, and (b) of FIG. 4 represents the clock signal. Furthermore, in (a) of FIG. 4, a square wave L1 represents the values of current output from the second buffer 27.

As illustrated in FIG. 4, when a predetermined voltage (for example, 1 V) obtained by dividing the power supply voltage VDD is applied from the first buffer 26 to the second buffer 27 under a condition other than normal operation, such as, before the clock signal is transmitted to the imaging unit 20, while the transmission of the clock signal is stopped, or at a time of starting up the endoscope system 1, the second buffer 27 is brought into an on-state. Thereby, the direct current is output at a predetermined level to the transmission cable 3 and it follows that current is consumed. This current consumption can prevent the high voltage of the power supply unit 61 from being applied to the imaging unit 20, due to a voltage drop of the transmission cable 3. Thereby, malfunction of the imaging unit 20, element breakage of the imaging unit 20, or the like can be reliably avoided.

According to an embodiment of the disclosure described above, the first buffer 26 applies a predetermined voltage to the second buffer 27 in a period in which the imaging unit 20 does not output the imaging signal to cause the second buffer 27 to output a predetermined direct current to the transmission cable 3, so that it is possible to prevent the high voltage from being applied to the imaging unit 20 under a condition other than the normal operation, such as, at a time of starting up, or while transmission of a pulse signal is stopped.

It should be noted that in an embodiment of the disclosure, the third transistor 266 includes the PMOS, and the second buffer 27 includes the NMOS, but the third transistor 266 may include an NMOS, and the second buffer 27 may include a PMOS.

According to some embodiments, it is possible to effectively prevent application of the high voltage to the imaging element when transmission of the pulse signal for driving the imaging element is stopped.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope configured to operate with a power supply voltage supplied from a processing device connected to the endoscope through a transmission cable, the endoscope comprising:
   a first chip including:
      an imaging sensor; and
      a first buffer configured to output an imaging signal generated by the imaging sensor; and
   a second chip including a second buffer configured to amplify the imaging signal being outputted from the first buffer and output the amplified imaging signal to the transmission cable,
   wherein the first buffer is configured to apply a predetermined voltage to the second buffer during a period in which the output of the imaging signal from the first buffer is stopped to cause the second buffer to output a direct current at a predetermined level to the transmission cable.

2. The endoscope according to claim 1, wherein the first buffer is configured to apply, to the second buffer, a voltage obtained by dividing a power supply voltage supplied from the processing device through the transmission cable.

3. The endoscope according to claim 1, wherein the first buffer is a PMOS source follower transistor including a constant current source configured to be driven by a voltage obtained by dividing a power supply voltage supplied from the processing device, a gate configured to receive input of the imaging signal, and a source connected to the second buffer.

4. An endoscope system comprising:
the endoscope according to claim 1; and
a processing device including a drive signal generator configured to transmit a drive signal to the imaging sensor through the transmission cable, an image processor configured to receive the imaging signal amplified by the second buffer through the transmission cable, and a power supply configured to supply a power supply voltage to the imaging sensor, the first chip, and the second chip through the transmission cable.

5. The endoscope according to claim 1, wherein the period in which the output of the imaging signal from the first buffer is stopped is before the first chip receives a clock signal.

6. The endoscope according to claim 1, wherein the period in which the output of the imaging signal from the first buffer is stopped is a period in which a transmission of clock signal to the first chip is stopped.

7. The endoscope according to claim 1, wherein the period in which the output of the imaging signal from the first buffer is stopped is during a start-up phase of the endoscope.

* * * * *